(12) United States Patent
Hirano et al.

(10) Patent No.: US 10,638,084 B2
(45) Date of Patent: Apr. 28, 2020

(54) ENDOSCOPE APPARATUS, ENDOSCOPE SYSTEM, AND ENDOSCOPE IMAGE RECORDING METHOD

(71) Applicant: OLYMPUS CORPORATION, Tokyo (JP)

(72) Inventors: Shinichiro Hirano, Hachioji (JP); Osamu Mitsunaga, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/935,564

(22) Filed: Mar. 26, 2018

(65) Prior Publication Data

US 2018/0288361 A1  Oct. 4, 2018

(30) Foreign Application Priority Data

Mar. 28, 2017  (JP) ................................ 2017-063384
Aug. 9, 2017   (JP) ................................ 2017-153846

(51) Int. Cl.
| | |
|---|---|
| *H04N 5/77* | (2006.01) |
| *A61B 1/00* | (2006.01) |
| *A61B 1/04* | (2006.01) |
| *G02B 23/24* | (2006.01) |
| *H04N 5/232* | (2006.01) |

(Continued)

(52) U.S. Cl.
CPC ........... *H04N 5/772* (2013.01); *A61B 1/0002* (2013.01); *A61B 1/0005* (2013.01); *A61B 1/00006* (2013.01); *A61B 1/00009* (2013.01); *A61B 1/00011* (2013.01); *A61B 1/00045* (2013.01); *A61B 1/00055* (2013.01); *A61B 1/00059* (2013.01); *A61B 1/00096* (2013.01); *A61B 1/00101* (2013.01); *A61B 1/00105* (2013.01); *A61B 1/00126* (2013.01); *A61B 1/00174* (2013.01); *A61B 1/04* (2013.01); *A61B 1/045* (2013.01); *G02B 23/2423* (2013.01); *G02B 23/2484* (2013.01); *H04N 5/23209* (2013.01); *H04N 5/77* (2013.01); *H04N 5/23293* (2013.01); *H04N 2005/2255* (2013.01)

(58) Field of Classification Search
None
See application file for complete search history.

(56) References Cited

U.S. PATENT DOCUMENTS

2007/0208252 A1* 9/2007 Makower ............. A61B 5/6851
                                                        600/424
2012/0187863 A1* 7/2012 Nonaka .............. H05B 33/0815
                                                        315/291

(Continued)

FOREIGN PATENT DOCUMENTS

JP     2000215209 A    8/2000

*Primary Examiner* — Eileen M Adams
(74) *Attorney, Agent, or Firm* — Scully, Scott, Murphy & Presser, P.C.

(57) ABSTRACT

An endoscope apparatus includes: an operation unit through which recording of an image acquired by an image pickup device can be instructed; and a controller configured to perform control to record, in a main recording unit, a first image acquired by the image pickup device when the image recording is instructed through the operation unit and record, in a sub recording unit, a second image acquired by the image pickup device irrespective of whether the image recording is instructed through the operation unit.

15 Claims, 13 Drawing Sheets

(51) Int. Cl.
*A61B 1/045* (2006.01)
*H04N 5/225* (2006.01)

(56) References Cited

U.S. PATENT DOCUMENTS

| | | | | |
|---|---|---|---|---|
| 2014/0375768 | A1* | 12/2014 | Tsuchiya | A61B 1/00163 348/45 |
| 2015/0272423 | A1* | 10/2015 | Ito | A61B 1/00009 600/476 |
| 2016/0048637 | A1* | 2/2016 | Nishiyama | A61B 1/00009 382/305 |

* cited by examiner

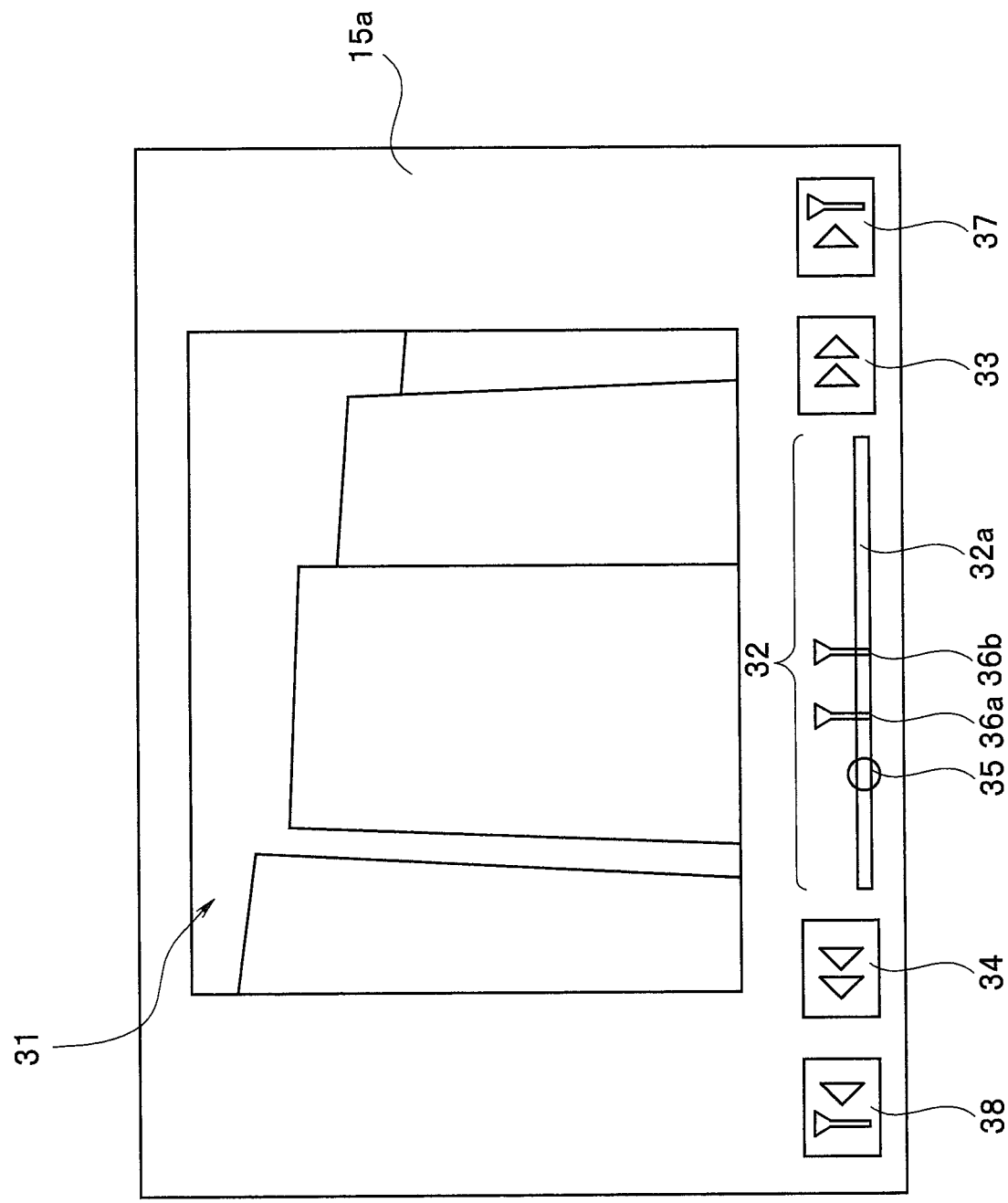

ENDOSCOPE APPARATUS, ENDOSCOPE SYSTEM, AND ENDOSCOPE IMAGE RECORDING METHOD

This application is based upon and claims the benefit of priority from the Japanese Patent Application No. 2017-63384 filed in Japan on Mar. 28, 2017 and Japanese Patent Application No. 2017-153846 filed in Japan on Aug. 9, 2017, the entire contents of which are incorporated herein by reference.

BACKGROUND

Technical Field

The present invention relates to an endoscope apparatus, an endoscope system, and an endoscope image recording method.

Background Art

Endoscope apparatuses are widely used in industrial and medical fields. In endoscope examination, an examiner inserts an insertion portion of an endoscope into an examination target, acquires an image of inside of the examination target through an observation window provided in a distal end portion of the insertion portion, and causes a display apparatus to display an endoscope image.

In addition, an examiner as a user of an endoscope apparatus can record an endoscope image in a storage apparatus by operating operation instruction members such as a freeze button and a record button during the examination. The recording of an endoscope image is performed for, for example, recording of an examination result or diagnosis after the examination.

As disclosed in, for example, Japanese Patent Application Laid-Open Publication No. 2000-215209, an endoscope apparatus including a plurality of image recording apparatuses for backup is also proposed.

Note that conventional endoscope image recording is performed only for a still image or a moving image, recording of which is instructed by a user through operation of a record instruction member such as a record button. Thus, for example, when recording of an endoscope image is missed, endoscope observation of a missed place needs to be performed again.

SUMMARY

An endoscope apparatus according to an aspect of the present invention includes: an operation unit through which recording of an image acquired by an image sensor can be instructed; and a controller configured to record, in a first storage, a first image acquired by the image sensor when image recording is instructed through the operation unit; and record, in a second storage, a second image acquired by the image sensor irrespective of whether the image recording is instructed through the operation unit.

An endoscope system according to another aspect of the present invention includes: the endoscope apparatus according to the present invention; and a server connected with the endoscope apparatus through a network. At least one of the first storage and the second storage is provided at the server.

An endoscope image recording method according to another aspect of the present invention includes: recording, in a first storage, a first image acquired by an image sensor when recording of an image acquired by the image sensor is instructed through an operation unit through which image recording can be instructed; and recording, in a second storage, a second image acquired by the image sensor irrespective of whether the image recording is instructed through the operation unit.

BRIEF DESCRIPTION OF THE DRAWINGS

FIG. 14 is a diagram illustrating an exemplary image at playback of a preliminarily recorded moving image according to the second to fifth embodiments of the present invention.

DETAILED DESCRIPTION OF PREFERRED EMBODIMENTS

Embodiments of the present invention will be described below with reference to the accompanying drawings.
(First Embodiment)
(Configuration)

Figure 1:
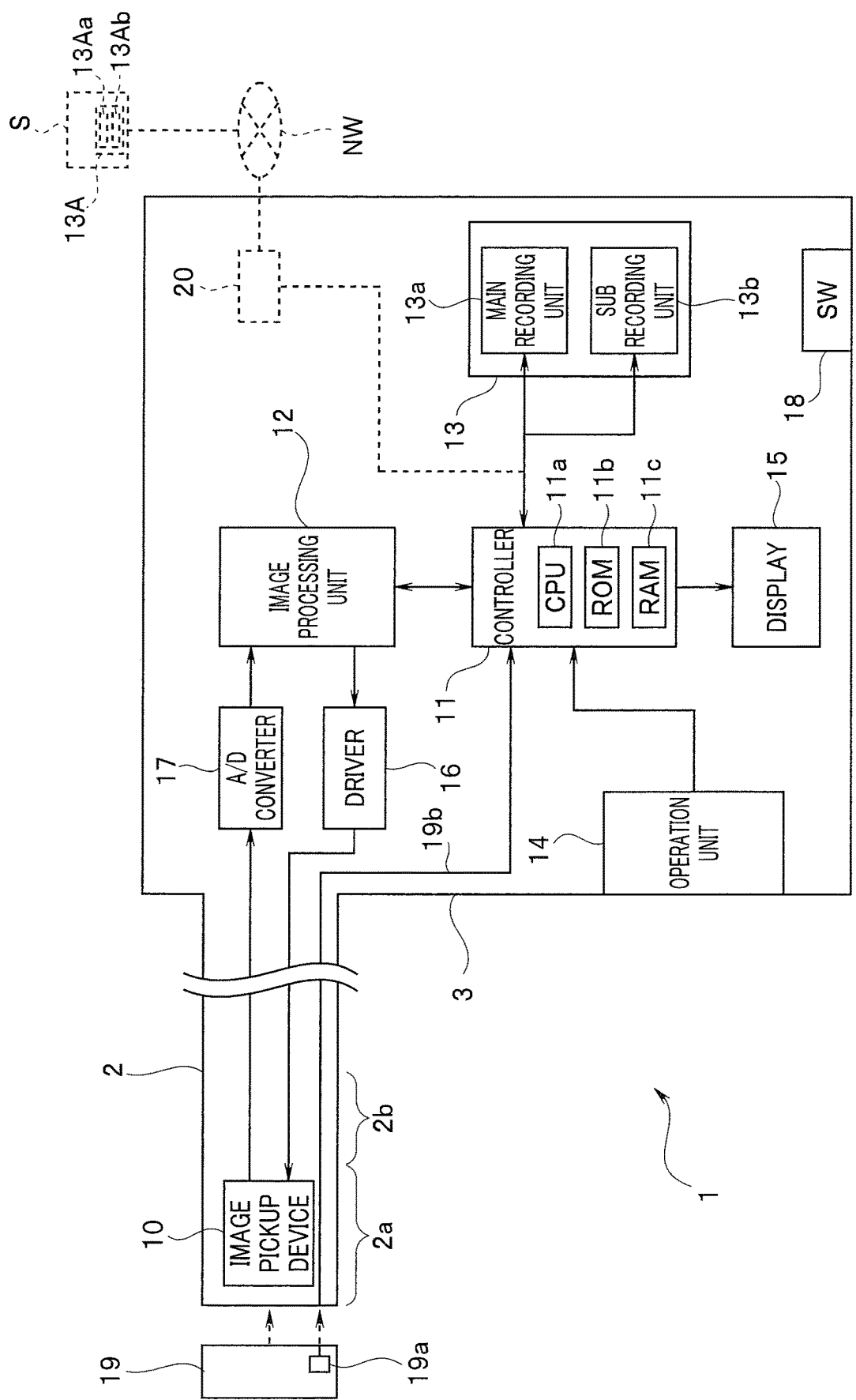
FIG. 1 is a configuration diagram illustrating a configuration of an endoscope apparatus according to a first embodiment of the present invention.

FIG. 1 is a configuration diagram illustrating a configuration of an endoscope apparatus according to the present embodiment. As illustrated in FIG. 1, this endoscope apparatus 1 includes an elongated insertion portion 2 and a body unit 3. The insertion portion 2 has a proximal end portion connected with the body unit 3.

The elongated insertion portion 2 is configured to be insertable into an examination target through a distal end portion 2a. A distal end rigid portion (not illustrated) is provided at the distal end portion 2a of the insertion portion 2, and an image pickup device 10 that is an image sensor is fixed to the distal end rigid portion. The image pickup device 10 configures an image sensor configured to acquire an image of inside of the examination target.

Note that a bending portion 2b is provided on a proximal end side of the distal end portion 2a. A user can bend the distal end portion 2a of the insertion portion 2 in four directions of up, down, right, and left directions by performing a bending operation through an operation unit 14 to be described later.

The body unit 3 includes a controller 11, an image processing unit 12, a storage 13, the operation unit 14, a display 15, a driver 16, and an analog-digital converter (hereinafter referred to as an A/D converter) 17.

The controller 11 controls operation of each component of the endoscope apparatus 1 in accordance with various kinds of functions of the endoscope apparatus 1. The controller 11 includes a central processing unit (hereinafter referred to as a CPU) 11a, a ROM 11b, and a RAM 11c.

Various computer programs are stored in the ROM 11b. The various kinds of functions of the endoscope apparatus 1 are achieved when the CPU 11a reads various computer programs from the ROM 11b, loads the programs onto the RAM 11c, and executes the programs based on an operation or instruction to the operation unit 14 by the user.

The image processing unit 12 is a circuit, for example, an FPGA (field programmable gate array) circuit, configured to drive the image pickup device 10 through the driver 16 based on a control signal from the controller 11, receive an image pickup signal from the image pickup device 10 through the A/D converter 17, and generate an endoscope image. The image processing unit 12 also performs, for example, noise removal processing and high dynamic range synthesis (HDR) processing on a generated image.

The storage 13 is a storage apparatus that can store data and configured of two storage media in the body unit 3 in this example. One of the storage media is a main recording unit 13a configured to record an image intentionally instructed by the user, and the other storage medium is a sub recording unit 13b configured to record an image irrespective of intention of the user. The main recording unit 13a and the sub recording unit 13b are each, for example, a flash memory. Image data of an endoscope image is recorded in the storage 13 under control of the controller 11.

When performing examination, the user mounts each storage medium onto a connector provided in the body unit 3.

Note that, although the storage 13 includes two recording units in this example, a storage region of one memory may be divided into virtual partitions to form the main recording unit 13a and the sub recording unit 13b. The storage media of the two recording units may be, for example, detachable memory cards.

As illustrated with dotted lines in FIG. 1, the endoscope apparatus 1 may include, instead of the storage 13, a communication unit 20 that is connectable to a communication network NW so that the controller 11 transmits image data of an endoscope image to an external storage apparatus connected with the communication network NW through the communication unit 20 and records the data in the external storage apparatus.

As illustrated with dotted lines in FIG. 1, a server S connected with the communication network NW such as the Internet includes a storage apparatus 13A. The storage apparatus 13A includes a first recording unit 13Aa corresponding to the main recording unit 13a described above, and a second recording unit 13Ab corresponding to the sub recording unit 13b described above. In this case, an endoscope system is configured by the endoscope apparatus 1 and the server S connected with the network NW.

Note that when the endoscope apparatus 1 includes either one of the main recording unit 13a and the sub recording unit 13b, the server S may include the first recording unit 13Aa or the second recording unit 13Ab corresponding to the recording unit not included in the endoscope apparatus 1. That is, the server S may include at least one of the first recording unit 13Aa and the second recording unit 13Ab.

The operation unit 14 includes a plurality of operation members. The plurality of operation members include, for example, a freeze button, a record button, and a bending operation instruction member.

For example, the user can display a still image generated from an image pickup signal from the image pickup device 10 on the display 15 by pressing the freeze button. In addition, the user can record a still image displayed on the display 15 in the main recording unit 13a of the storage 13 by pressing the record button. Accordingly, the operation unit 14 is an operation unit through which recording of an image acquired by the image pickup device 10 as the image sensor can be instructed.

In addition, the operation unit 14 includes a button for any other function to allow the user to instruct, for example, playback of an image recorded in the storage 13.

The display 15 is a display apparatus, such as a liquid crystal display, configured to display an image acquired by the image pickup device 10. The display 15 displays, for example, a menu screen for performing various settings in addition to an endoscope image generated by the image processing unit 12.

The driver 16 is a circuit configured to generate various drive signals for driving the image pickup device 10 and supply the signals to the image pickup device 10.

The A/D converter 17 is a circuit configured to receive an image pickup signal that is an analog signal from the image pickup device 10, convert the analog signal into a digital signal, and output the digital signal to the image processing unit 12.

The body unit 3 is provided with a power switch 18 so that the user can activate the endoscope apparatus 1 by turning on the power switch 18 or stop the endoscope apparatus 1 by turning off the power switch 18.

An optical adapter 19 is attachable to the distal end portion 2a of the insertion portion 2. The optical adapter 19 is an instrument for changing, for example, the direction of a visual field and the angle of view. The user selects the optical adapter 19 in accordance with, for example, an examination target and an examination method, and mounts the optical adapter 19 onto the distal end portion 2a.

The optical adapter 19 includes a built-in identification information storage 19a. The identification information storage 19a is a non-volatile memory storing information on the type of the optical adapter 19. When the optical adapter 19 is mounted on the distal end portion 2a of the insertion portion 2, the controller 11 can read information on the type of the identification information storage 19a through a signal line 19b.

Note that identification information does not necessarily need to be used for identification of the optical adapter 19. For example, the optical adapter 19 may be provided with a resistor having a resistance value in accordance with a type of the optical adapter 19 so that the optical adapter 19 is identified by detecting the resistance value of the resistor at the body unit 3.

The user can record a still image or a moving image in the main recording unit 13a by instructing recording of an endoscope image through operation of the operation unit 14, and also play back an image recorded in the main recording unit 13a or the sub recording unit 13b and display the image on the display 15 through operation of the operation unit 14.

(Effects)

The following describes image record processing in the sub recording unit 13b in the endoscope apparatus 1.

Figure 2:
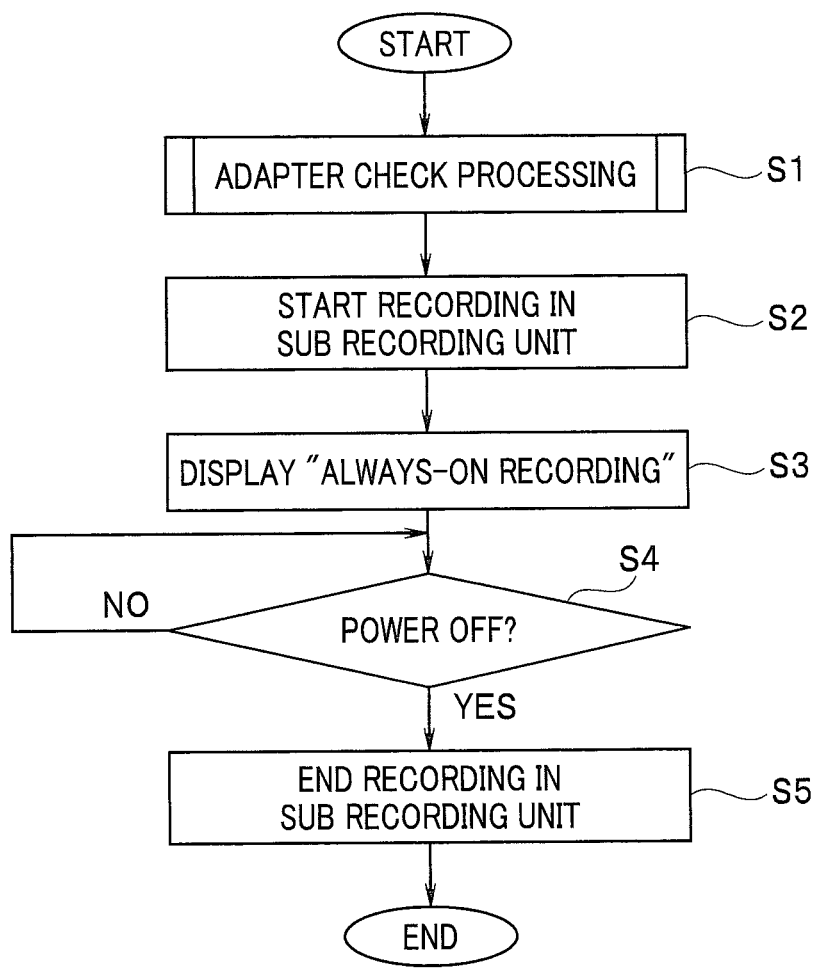
FIG. 2 is a flowchart illustrating an exemplary process of record processing in a sub recording unit 13*b* after an endoscope apparatus 1 is turned on according to the first embodiment of the present invention.

FIG. 2 is a flowchart illustrating an exemplary process of record processing in the sub recording unit 13b after the endoscope apparatus 1 is turned on.

When the power switch 18 of the endoscope apparatus 1 is turned on, the controller 11 reads, from the ROM 11b, a preliminary record processing program that executes the processing illustrated in FIG. 2, and executes the program.

The user brings the endoscope apparatus 1 to a position where an examination target is placed, and performs endoscope examination of the examination target. When starting the examination, the user turns on the endoscope apparatus 1.

The controller 11 first executes adapter check processing (step (hereinafter abbreviated as "S") 1).

Before or after turning on the endoscope apparatus 1, the user mounts the optical adapter 19 in accordance with, for example, the examination target onto the distal end portion 2a of the insertion portion 2.

In the adapter check processing, the controller 11 reads type information held by the optical adapter 19 from the identification information storage 19a and checks, for example, whether an optical adapter appropriate for an examination purpose is mounted on the distal end portion 2a.

For example, when the correct optical adapter 19 is not mounted on the distal end portion 2a, the display 15 displays a message for prompting mounting of the correct optical adapter to the user.

When the correct optical adapter 19 is mounted and the endoscope apparatus 1 becomes ready for performing endoscope examination through the adapter check processing, a live image is displayed on the display 15.

More specifically, the controller 11 drives the driver 16 and outputs a control signal to the image processing unit 12 to generate an endoscope image based on an image pickup signal from the image pickup device 10. Having received the endoscope image from the image processing unit 12, the controller 11 outputs the endoscope image to the display 15. As a result, an image of inside of the examination target picked up by the image pickup device 10, that is, an endoscope image is displayed as a live image on the display 15.

After S1, the controller 11 starts recording of a live image in the sub recording unit 13b (S2). That is, when the endoscope apparatus 1 becomes ready for performing endoscope examination and displaying a live image, recording of an endoscope image (moving image) in the sub recording unit 13b is started in background.

After S2, the controller 11 performs predetermined display indicating that the live image is being preliminarily recorded as a moving image in background (S3). The predetermined display indicating "in preliminary recording" is display for notifying the user that the live image is being preliminarily recorded in background.

Although FIG. 2 only illustrates preliminary recording of a live image in the endoscope apparatus 1, that is, the processing of image recording of a moving image to the sub recording unit 13b, the user can operate the operation unit 14 to record a still image or a moving image after S3, that is, during examination. Endoscope image record processing in response to an instruction by the user will be described later.

When the examination ends, the user turns off the power switch 18 of the endoscope apparatus 1. Then, the controller 11 determines whether the endoscope apparatus 1 is turned off (S4).

The controller 11 performs no processing when the endoscope apparatus 1 is not turned off (NO at S4).

When the endoscope apparatus 1 is turned off (YES at S4), the controller 11 ends the recording in the sub recording unit 13b (S5).

The following describes processing of recording a still image or a moving image based on an instruction by the user during examination.

Figure 3:
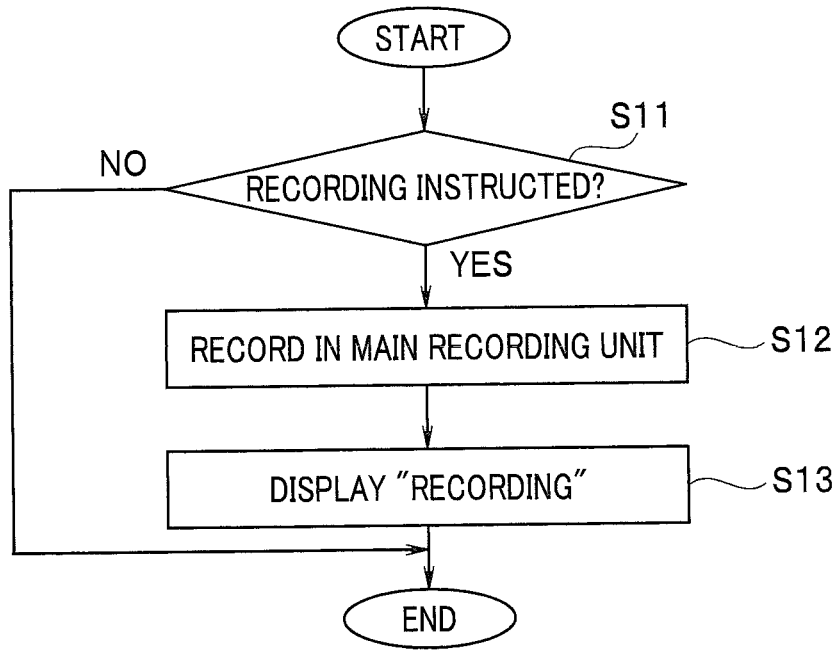
FIG. 3 is a flowchart illustrating an exemplary process of record processing in a main recording unit 13*a* in accordance with an image record instruction through an operation unit 14 according to the first embodiment of the present invention.

FIG. 3 is a flowchart illustrating an exemplary process of record processing in the main recording unit 13a in accordance with an image record instruction through the operation unit 14. As described above, the processing illustrated in FIG. 3 is executed between S3 and S4 illustrated in FIG. 2.

The controller 11 determines whether a record instruction is performed through the operation unit 14 (S11).

At still image recording, the user performs record instruction by pressing the freeze button while a live image is displayed on the display 15, and then pressing the record button (REC button) of the operation unit 14. That is, at S11, the controller 11 determines whether a still image record instruction is performed by determining whether the freeze button of the operation unit 14 is pressed while a live image is displayed on the display 15, and then the record button is pressed.

At moving image recording, the user performs a record instruction by pressing the record button (REC button) while a live image is displayed on the display 15. Thus, the controller 11 determines whether a moving image record instruction is performed by determining whether the record button is pressed while a live image is displayed on the display 15. Recording of a moving image is started when the record button is pressed, and the recording of a moving image is ended when a stop button is pressed.

When no record instruction is performed (NO at S11), the controller 11 performs no processing. When the record instruction is performed (YES at S11), the controller 11 performs recording in the main recording unit 13a (S12). In a case of still image, the controller 11 records an image being frozen in the main recording unit 13a. In a case of a moving image, once the record button is pressed, the record instruction is performed (YES at S11) until the stop button is pressed, and accordingly, the controller 11 records a live image in the main recording unit 13a.

After S12, the controller 11 performs display processing (S13). At S13, when a moving image is being recorded, processing of displaying, on the display 15, a mark or the like indicating that the image is being recorded is performed.

An endoscope image of a still image or a moving image intended by the user is recorded in the main recording unit 13a through the processing illustrated in FIG. 3, and simultaneously, an endoscope image of a moving image unrelated to photographing intention of the user is recorded in the sub recording unit 13b through the processing illustrated in FIG. 2.

That is, when image recording is instructed by the user through the operation unit 14, the controller 11 performs control to record a still image or a moving image that is an image acquired by the image pickup device 10 in the main recording unit 13a as a first storage and record a moving image acquired by the image pickup device 10, irrespective of whether image recording is instructed by the user through the operation unit 14, in the sub recording unit 13b as a second storage.

Figure 4:
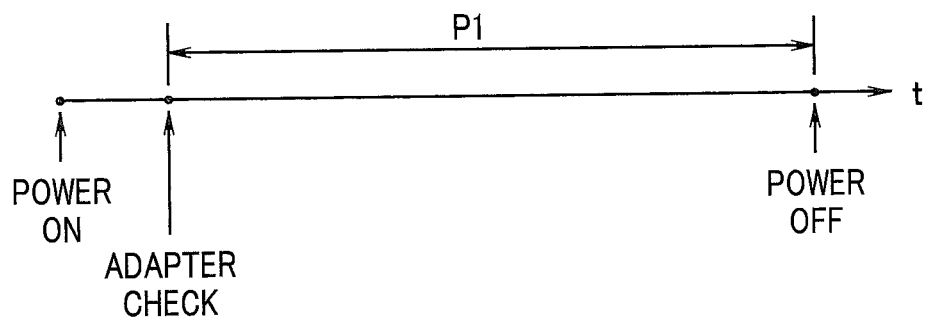
FIG. 4 is a time chart illustrating a duration of recording of an endoscope image (moving image) in the sub recording unit 13*b* until the endoscope apparatus 1 is turned off after the endoscope apparatus 1 is turned on according to the first embodiment of the present invention.

FIG. 4 is an exemplary time chart illustrating a duration of recording of an endoscope image (moving image) in the sub recording unit 13b until the endoscope apparatus 1 is turned off after the endoscope apparatus 1 is turned on.

Recording of an endoscope image as a live image in the sub recording unit 13b is not performed until the power switch 18 of the endoscope apparatus 1 is turned on and the optical adapter 19 is checked through the adapter check processing (S1) as time t elapses. When the optical adapter 19 is checked, recording of a live image in the sub recording unit 13b is started, and the recording continues until the power switch 18 is turned off.

That is, the controller 11 performs control to record a live image in the sub recording unit 13b after the processing of checking the optical adapter 19 mounted on the distal end portion 2a of the insertion portion 2 of the endoscope apparatus 1. Accordingly, recording of an endoscope image (moving image) in the sub recording unit 13b is performed in a duration P1 until the power switch 18 is turned off after the optical adapter 19 is checked as illustrated in FIG. 4. In other words, an endoscope image (moving image) is always recorded in the sub recording unit 13b in the duration P1. The duration P1 corresponds to an entire recording time during which an endoscope image as a moving image is preliminarily recorded in the sub recording unit 13b.

Then, the controller 11 records all live images acquired by the image pickup device 10 in the sub recording unit 13b. Accordingly, a live image before the user inserts the distal end portion 2a of the insertion portion 2 into the examination target is recorded, and thus it is possible to check, after examination, how and from where the distal end portion 2a is inserted into the examination target.

Figure 5:
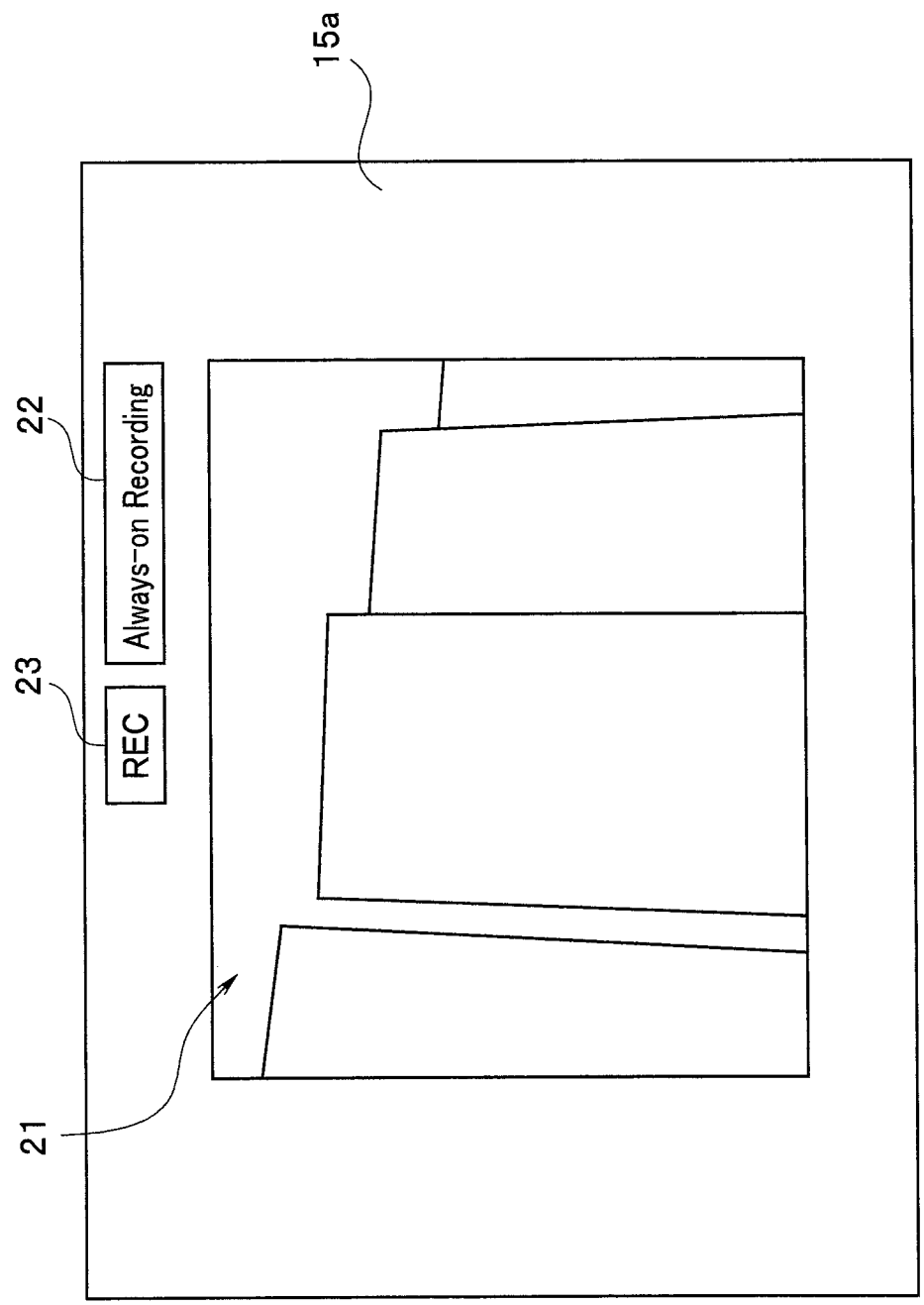
FIG. 5 is a diagram illustrating an exemplary display screen of a display 15 according to the first embodiment of the present invention.

FIG. 5 is a diagram illustrating an exemplary display screen of the display 15.

An image display region 21 in which an endoscope image is displayed is displayed on a display screen 15a of the display 15.

An endoscope image as what is called a live image is displayed in the image display region 21 at normal observation. The user performs endoscope examination while watching the live image.

As described above, display indicating that image recording in the sub recording unit 13b is performed, in this example, display 22 of "Always-on Recording" indicating "in preliminary recording" is displayed on the display screen 15a in the duration P1. Note that display of a predetermined mark may be performed in place of the display 22.

That is, when a live image is being recorded in the sub recording unit 13b, the controller 11 displays, on the display 15, a character or a mark for notifying the user that the live image is being recorded in the sub recording unit 13b.

When recording of a moving image is instructed to the operation unit 14 by intention of the user, "REC" display 23 indicating that the moving image is being recorded is displayed on the display screen 15a. Note that display of a predetermined mark may be performed in place of the "REC" display.

That is, when a moving image is being recorded in the main recording unit 13a, the controller 11 displays, on the display 15, a character or a mark for notifying the user that the moving image is being recorded in the main recording unit 13a.

While a moving image is being recorded by an instruction from the user, the user can recognize that a live image is being recorded in background based on display of "On Reserved-Recording" indicating "in preliminary recording".

When examination with the endoscope apparatus 1 ends, the user can remove the two memory cards from the body unit 3, mount each memory card on a PC or the like, and cause a monitor to display an endoscope image recorded in the memory card or use the endoscope image to make an examination report.

The user can operate the operation unit 14 of the endoscope apparatus 1 to cause the display 15 to display a predetermined menu screen, copy image data of a preliminary record in the sub recording unit 13b to the main recording unit 13a, and delete the image data.

As described above, the above-described embodiment provides an endoscope apparatus, an endoscope system, and an endoscope image recording method that allow check of an examination place without performing operation for observation again, for example, when recording of an image of the examination place is missed.

In addition, the user can check a situation of any place examined so far halfway through examination by playing back an image recorded in the sub recording unit 13b and causing the display 15 to display the image.

Since all live images during examination are recorded in the sub recording unit 13b, it is possible to check later how a plurality of examination places are reached, that is, an insertion path when the examination target has a complicate structure, and thus the user can check an examination procedure at next examination.

The following describes other embodiments.

Although preliminary recording of an endoscope image is performed until the endoscope apparatus 1 is turned off after the endoscope apparatus 1 becomes ready for displaying a live image in the above-described first embodiment, no recording of a moving image in the sub recording unit may be performed under a predetermined examination situation.

The following describes a plurality of embodiments in which preliminary recording of an endoscope image is not performed under such a predetermined examination situation.

(Second Embodiment)

In the endoscope apparatus according to the first embodiment, preliminary recording of an endoscope image is started when the endoscope apparatus 1 is turned on and becomes ready for displaying a live image, and the preliminary recording of an endoscope image ends when the endoscope apparatus 1 is turned off and examination ends. However, in a second embodiment, the preliminary recording is not started when the endoscope apparatus 1 is turned on and becomes ready for displaying a live image, but the preliminary recording of an endoscope image is started after the distal end portion 2a of the insertion portion 2 is inserted into an examination target, and the preliminary recording of an endoscope image ends when the distal end portion 2a of the insertion portion 2 is removed from the examination target.

The endoscope apparatus according to the present embodiment has a similar configuration to the configuration of the endoscope apparatus 1 according to the first embodiment (FIG. 1). Thus, any identical component is denoted by an identical reference sign, and description thereof will be omitted, whereas any different configuration will be described.

Figure 6:
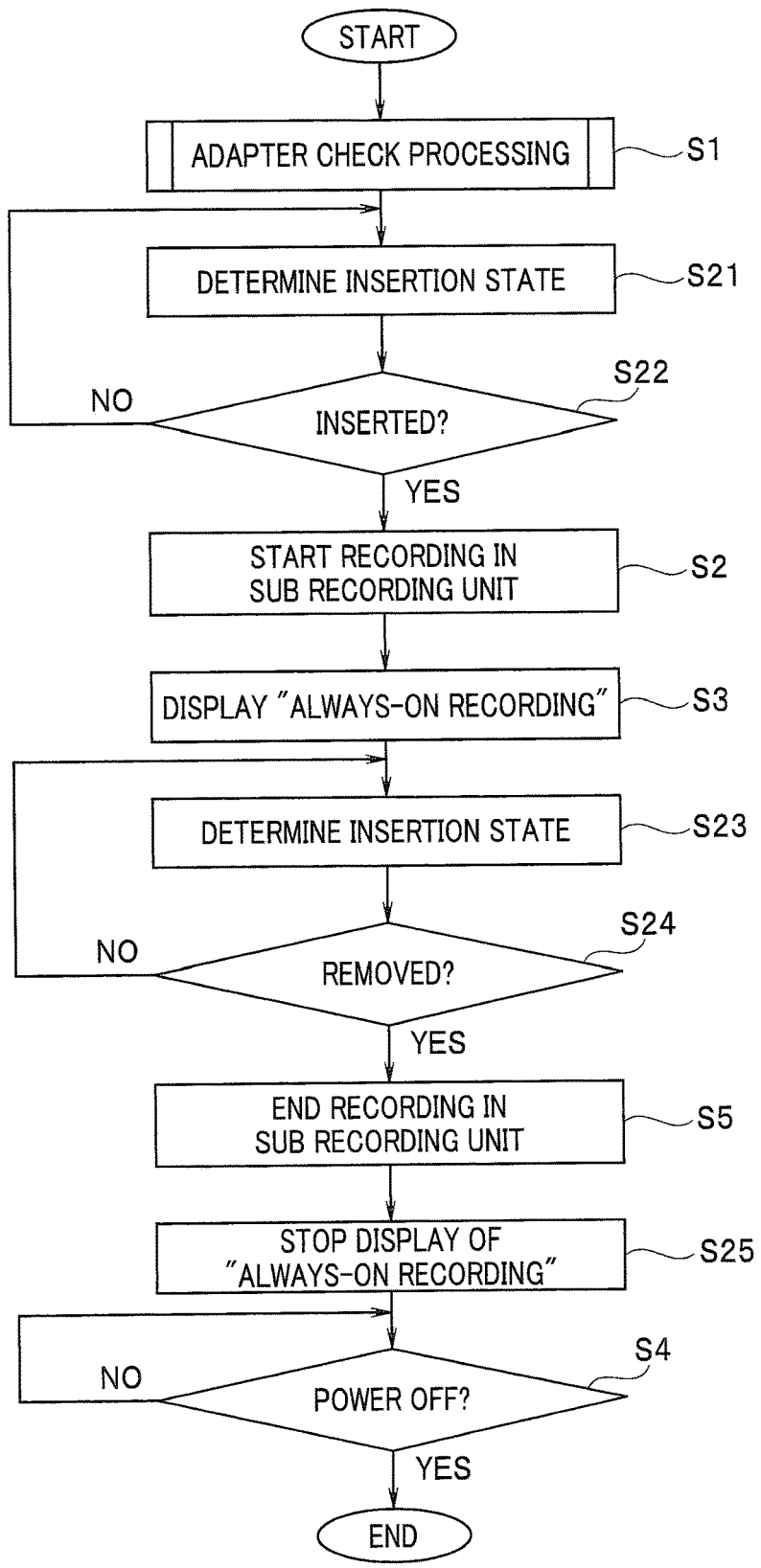
FIG. 6 is a flowchart illustrating an exemplary process of record processing in the sub recording unit 13*b* after the endoscope apparatus 1 is turned on according to a second embodiment of the present invention.

FIG. 6 is a flowchart illustrating an exemplary process of record processing in the sub recording unit 13b after the endoscope apparatus 1 is turned on according to the present embodiment.

When the power switch 18 of the endoscope apparatus 1 is turned on, the controller 11 reads a preliminary record processing program that executes processing illustrated in FIG. 6 from the ROM 11b and executes the program. The following describes the processing illustrated in FIG. 6 while description of any processing the same as the processing illustrated in FIG. 2 is simplified.

When the correct optical adapter 19 is mounted and the endoscope apparatus 1 becomes ready for performing endoscope examination through the adapter check processing (S1), a live image is displayed on the display 15.

After S1, the controller 11 executes insertion state determination in which an insertion state of the insertion portion 2 is determined (S21).

At S21, the controller 11 analyzes the live image to determine whether the distal end portion 2a of the insertion portion 2 is inserted in the examination target based on the live image. Brightness of the live image largely changes when the distal end portion 2a is inserted into the examination target. The live image is bright at a place where examination is performed since the place is illuminated with, for example, indoor illumination, but the live image is dark when the distal end portion 2a of the insertion portion 2 is inserted in the examination target because no illumination is provided.

Thus, the controller 11 can determine whether the distal end portion 2a of the insertion portion 2 is inserted in the examination target based on whether the brightness of the live image is equal to or larger than a predetermined value from a luminance value of each pixel of the live image from the image processing unit 12.

The controller 11 determines whether the insertion portion 2 is inserted in the examination target based on a result of the determination at S21 (S22). When the insertion portion 2 is not inserted (NO at S22), the process returns to S21.

When it is determined that the insertion portion 2 is inserted in the examination target based on the result of the determination at S21 (YES at S22), the controller 11 starts recording of a live image in the sub recording unit 13b (S2) and performs display processing indicating "in preliminary recording" (S3).

That is, when the distal end portion 2a of the insertion portion 2 is inserted into the examination target, recording of an endoscope image (moving image) in the sub recording unit 13b is started.

After S3, the controller 11 executes the insertion state determination in which an insertion state of the insertion portion 2 is determined (S23).

At S23, the controller 11 analyzes the live image to determine whether the insertion portion 2 is removed from the inside of the examination target based on the live image. When the insertion portion 2 is removed from the inside of the examination target, the brightness of the live image largely changes and the live image becomes bright. Thus, the controller 11 can determine that the distal end portion 2a of the insertion portion 2 is removed from the inside of the examination target when the brightness of the live image is equal to or larger than a predetermined value based on the luminance value of each pixel of the live image from the image processing unit 12.

At S24, when it is determined that the distal end portion 2a of the insertion portion 2 is removed from the inside of the examination target (YES at S24), the controller 11 ends recording of the live image in the sub recording unit 13b (S5) and stops the display of "in preliminary recording" (S25).

After S25, when the endoscope apparatus 1 is turned off, the process ends.

As described above, the processing at S21 and S23 configures an examination situation determination unit configured to determine a examination situation by the user. The controller 11 performs control to record the live image in the sub recording unit 13b based on the examination situation determined by the examination situation determination unit.

In the present embodiment, the examination situation determination unit of S21 and S23 is an insertion state determination unit configured to determine whether the distal end portion 2a of the insertion portion 2 of the endoscope apparatus 1 is inserted in the examination target.

The examination situation by the user is a state indicating whether the distal end portion 2a is inserted in the examination target. When it is determined by the insertion state determination unit that the distal end portion 2a is inserted in the examination target, the controller 11 records a live image acquired by the image pickup device 10 in the sub recording unit 13b.

Note that the processing of recording of a still image and recording of a moving image in accordance with an instruction from the user during examination is the same as the processing in the first embodiment.

Figure 7:
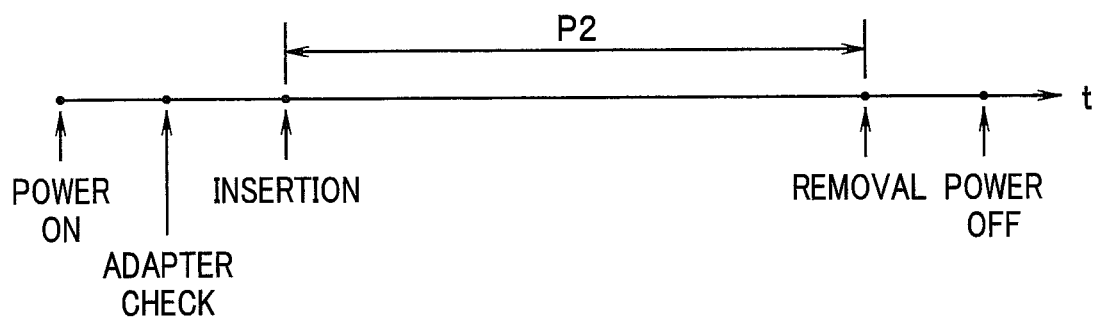
FIG. 7 is a time chart illustrating the duration of recording of an endoscope image (moving image) in the sub recording unit 13*b* until the endoscope apparatus 1 is turned off after the endoscope apparatus 1 is turned on according to the second embodiment of the present invention.

FIG. 7 is an exemplary time chart illustrating the duration of recording of an endoscope image (moving image) in the sub recording unit 13b until the endoscope apparatus 1 is turned off after the endoscope apparatus 1 is turned on.

Recording of an endoscope image in the sub recording unit 13b is not performed until the power switch 18 of the endoscope apparatus 1 is turned on and the distal end portion 2a of the insertion portion 2 is inserted into the examination target as time t elapses. Recording of an endoscope image in the sub recording unit 13b is started when the distal end portion 2a is inserted into the examination target, and the recording continues until the distal end portion 2a of the insertion portion 2 is removed from the inside of the examination target.

That is, as illustrated in FIG. 7, recording of an endoscope image (moving image) in the sub recording unit 13b is performed in a duration P2 until the distal end portion 2a is removed from the inside of the examination target after the distal end portion 2a is inserted into the examination target. The duration P2 corresponds to the entire recording time during which an endoscope image as a moving image is preliminarily recorded in the sub recording unit 13b.

As described above, the above-described embodiment can provide an endoscope apparatus, an endoscope system, and an endoscope image recording method that allow check of an examination place without performing operation for observation again, for example, when recording of an image of the examination place is missed.

Note that although whether the insertion portion 2 is inserted in the examination target is determined based on the brightness of an endoscope image in the second embodiment described above, whether the insertion portion 2 is inserted in the examination target may be determined by any other method.

For example, as disclosed in Japanese Patent Application Laid-Open Publication No. 2015-196045, a sensor may be provided to a grasping portion of the endoscope apparatus 1 to determine whether the insertion portion 2 is inserted in the examination target or an insertion operation is started by determining whether the user is grasping the grasping portion, or an acceleration sensor may be provided in the distal end portion 2a to detect motion of the distal end portion 2a based on an output signal from the acceleration sensor and determine whether the insertion portion 2 is inserted in the examination target or an insertion operation is started by determining whether the motion is equal to or larger than a predetermined threshold.

(Third Embodiment)

In the endoscope apparatus according to the first embodiment, preliminary recording of an endoscope image is started when the endoscope apparatus 1 is turned on and becomes ready for displaying a live image, and the preliminary recording of an endoscope image ends when the endoscope apparatus 1 is turned off and examination ends. However, in a third embodiment, the preliminary recording is not started when the endoscope apparatus 1 is turned on and becomes ready for displaying a live image, but the preliminary recording of an endoscope image is performed only while the live image is displayed on the display 15, and the preliminary recording of an endoscope image is not performed when no live image is displayed on the display 15.

The endoscope apparatus according to the present embodiment has a similar configuration to the configuration of the endoscope apparatus 1 according to the first and second embodiments (FIG. 1). Thus, any identical component is denoted by an identical reference sign, and description thereof will be omitted, whereas any different configuration will be described.

Figure 8:
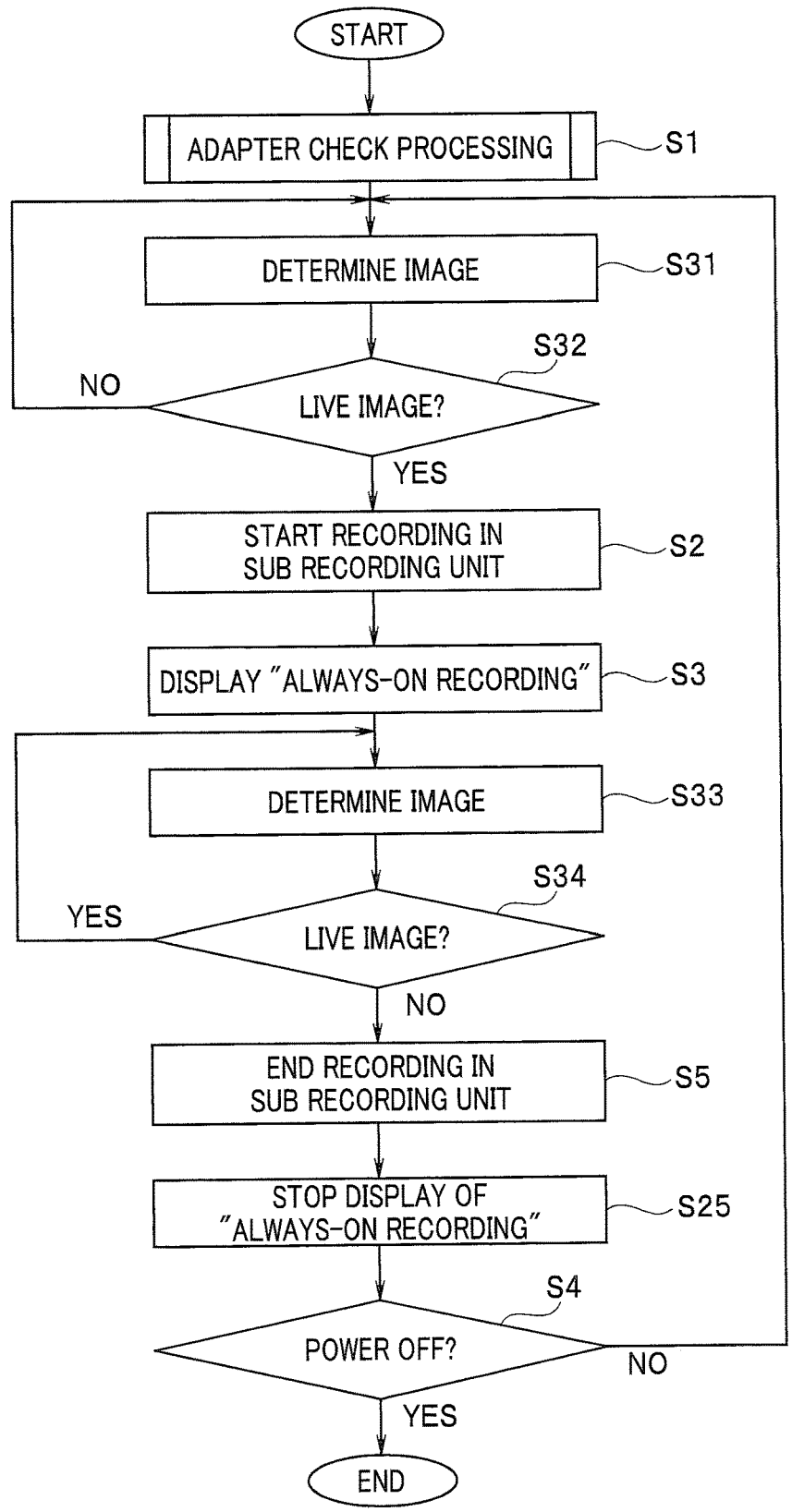
FIG. 8 is a flowchart illustrating an exemplary process of record processing in the sub recording unit 13*b* after the endoscope apparatus 1 is turned on according to a third embodiment of the present invention.

FIG. 8 is a flowchart illustrating an exemplary process of record processing in the sub recording unit 13b after the endoscope apparatus 1 is turned on according to the present embodiment.

When the power switch 18 of the endoscope apparatus 1 is turned on, the controller 11 reads a preliminary record processing program that executes processing illustrated in FIG. 8 from the ROM 11b and executes the program. The following describes the processing illustrated in FIG. 8 while description of any processing the same as the processing illustrated in FIGS. 2 and 6 is simplified.

When the correct optical adapter 19 is mounted and the endoscope apparatus 1 becomes ready for performing endoscope examination through the adapter check processing (S1), a live image is displayed on the display 15.

After S1, the controller 11 executes image determination (S31).

At S31, the controller 11 determines whether an image outputted to the display 15 is a live image.

When the user operates the operation unit 14 to cause the display 15 to display a menu screen, the menu screen is displayed on the display screen 15a of the display 15 in place of the live image. The user can perform various settings, setting change, setting check, and the like through the menu screen. In such a case, no live image is displayed on the display 15.

When a measurement function is used, too, a measurement screen is displayed on the display 15, but no live image is displayed.

When the freeze button is pressed to cause the display 15 to display a still image, too, no live image is displayed.

The controller 11 can receive a menu screen display instruction from the user and determine whether the menu screen and, for example, a various setting screen to which the screen is transitioned are outputted to the display 15. Similarly, the controller 11 can receive a measurement function execution instruction from the user and determine whether, for example, the measurement screen is outputted to the display 15.

The controller 11 determines whether a live image is displayed on the display 15 based on a result of the determination at S31 (S32). When no live image is displayed on the display 15 (NO at S32), the process returns to S31.

When it is determined that a live image is displayed on the display 15 based on the result of the determination at S31 (YES at S32), the controller 11 starts recording of a live image in the sub recording unit 13b (S2) and performs display processing indicating "in preliminary recording" (S3).

That is, recording of an endoscope image (moving image) in the sub recording unit 13b is performed when a live image is displayed on the display 15.

After S3, the controller 11 executes image determination the same as the image determination at S31 (S33), and determines whether a live image is displayed on the display 15 (S34). When a live image is displayed on the display 15 (YES at S34), the process returns to S33.

At S34, when it is determined that no live image is displayed on the display 15 (NO at S34), the controller 11 ends recording of a live image in the sub recording unit 13b (S5) and stops the display of "in preliminary recording" (S25).

After S25, when the endoscope apparatus 1 is turned off, the process ends. When the endoscope apparatus 1 is not turned off (NO at S4), the process returns to S31.

As described above, the processing at S31 and S33 configures an examination situation determination unit configured to determine a examination situation by the user. The controller 11 performs control to record a live image in the sub recording unit 13b based on the examination situation determined by the examination situation determination unit.

In the present embodiment, the examination situation determination unit of S31 and S33 is a live image determination unit configured to determine whether an image displayed on the display 15 is a live image.

The examination situation by the user is a state indicating whether an image displayed on the display 15 is a live image. When it is determined by the live image determination unit that an image displayed on the display 15 is a live image, the controller 11 records a live image acquired by the image pickup device 10 in the sub recording unit 13b.

Note that the processing of recording of a still image and recording of a moving image in accordance with an instruction from the user during examination is the same as the processing in the first embodiment.

Figure 9:
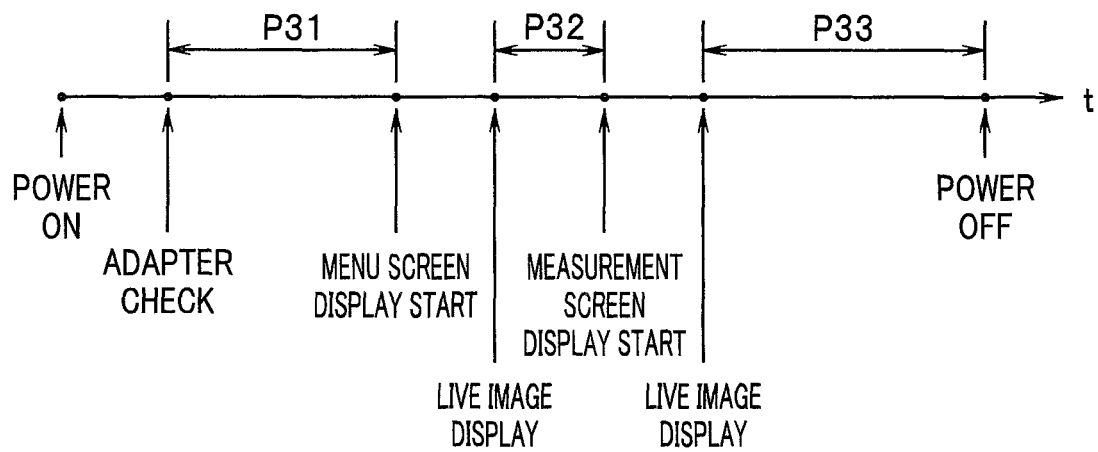
FIG. 9 is a time chart illustrating the duration of recording of an endoscope image (moving image) in the sub recording unit 13*b* until the endoscope apparatus 1 is turned off after the endoscope apparatus 1 is turned on according to the third embodiment of the present invention.

FIG. 9 is an exemplary time chart illustrating the duration of recording of an endoscope image (moving image) in the sub recording unit 13b until the endoscope apparatus 1 is turned off after the endoscope apparatus 1 is turned on.

As illustrated in FIG. 9, recording of an endoscope image in the sub recording unit 13b is performed after the power switch 18 of the endoscope apparatus 1 is turned on and the optical adapter 19 is checked as time t elapses. The recording of an endoscope image in the sub recording unit 13b stops when the user causes the display 15 to display a menu screen to perform, for example, setting change. Thus, recording of an endoscope image in the sub recording unit 13b is performed in a duration P31 until the menu screen is displayed after the adapter check.

When the display of the menu screen ends, a live image is displayed on the display 15, and recording of an endoscope image in the sub recording unit 13b is resumed.

Thereafter, when the user instructs a measurement function to perform distance measurement by specifying measurement points on a screen, the measurement screen is displayed on the display 15. When the measurement screen is displayed, the recording of an endoscope image in the sub recording unit 13b stops. Then, when the user instructs live screen display, a live image is displayed on the display 15, and recording of an endoscope image in the sub recording unit 13b is resumed.

Thus, recording of an endoscope image in the sub recording unit 13b is performed in a duration P32 until the measurement screen is displayed after the live image is displayed following end of the display of the menu screen.

When the display of the measurement screen ends, a live image is displayed on the display 15, and recording of an endoscope image in the sub recording unit 13b is resumed. As illustrated in FIG. 9, recording of an endoscope image in the sub recording unit 13b is performed in a duration P33 until the endoscope apparatus 1 is turned off after the display of the measurement screen ends. A sum of the durations P31, P32, and P33 corresponds to the entire recording time during which an endoscope image as a moving image is preliminarily recorded in the sub recording unit 13b.

As described above, the above-described embodiment can provide an endoscope apparatus, an endoscope system, and an endoscope image recording method that allow check of an examination place without performing operation for observation again, for example, when recording of an image of the examination place is missed.

(Fourth Embodiment)

In the endoscope apparatus according to the first embodiment, preliminary recording of an endoscope image is started when the endoscope apparatus 1 is turned on and becomes ready for displaying a live image, and the preliminary recording of an endoscope image ends when the endoscope apparatus 1 is turned off and examination ends. However, in a fourth embodiment, preliminary recording of an endoscope image is not performed when the endoscope apparatus 1 is turned on and becomes ready for displaying a live image but a change amount of an image is not within a predetermined range, for example, when the distal end portion makes no motion or extremely small motion or is moving extremely fast halfway through examination.

The endoscope apparatus according to the present embodiment has a similar configuration to the configuration of the endoscope apparatus 1 according to the first to third embodiments (FIG. 1). Thus, any identical component is denoted by an identical reference sign, and description thereof will be omitted, whereas any different configuration will be described.

Figure 10:
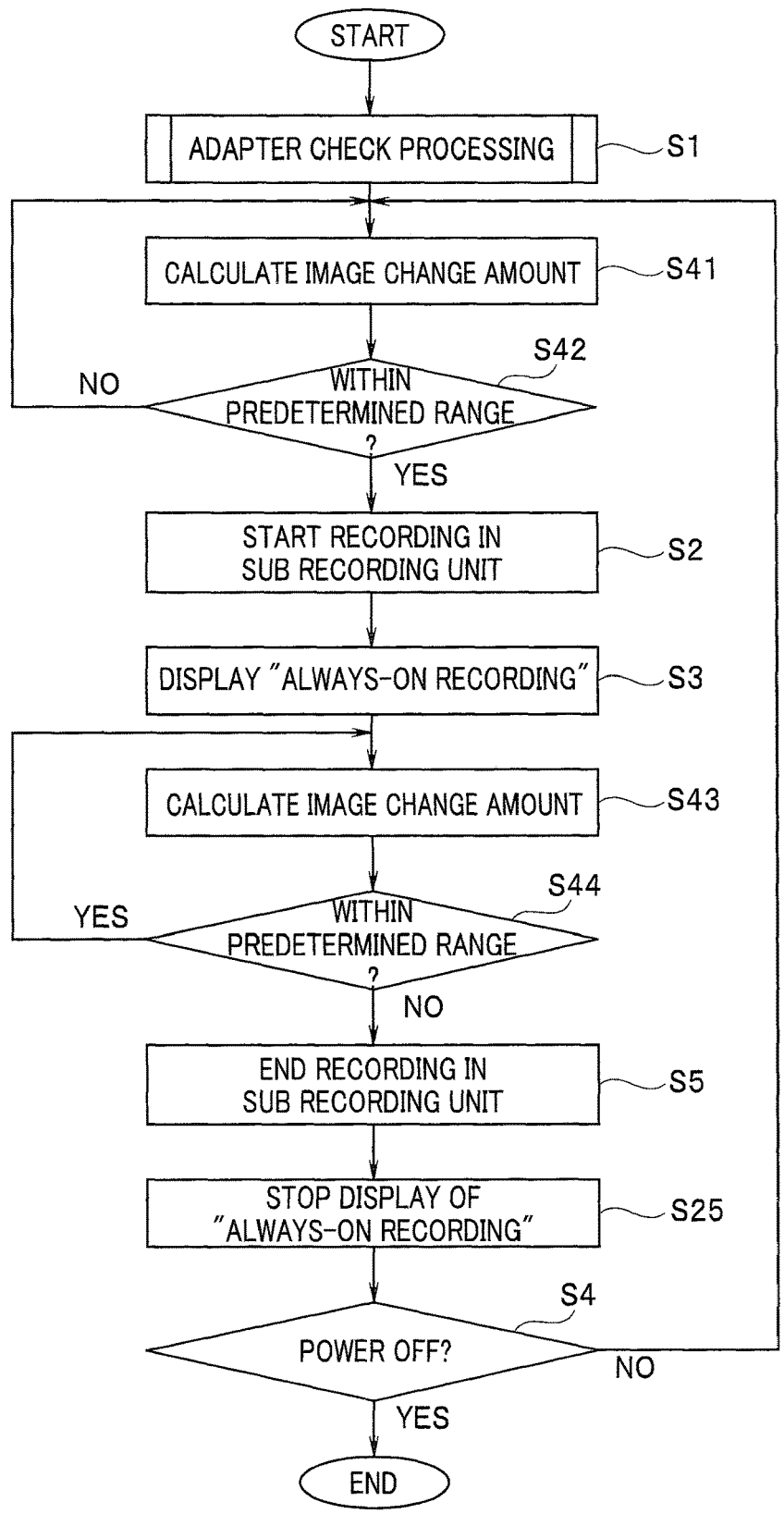
FIG. 10 is a flowchart illustrating an exemplary process of record processing in the sub recording unit 13*b* after the endoscope apparatus 1 is turned on according to a fourth embodiment of the present invention.

FIG. 10 is a flowchart illustrating an exemplary process of record processing in the sub recording unit 13b after the endoscope apparatus 1 is turned on according to the present embodiment.

When the power switch 18 of the endoscope apparatus 1 is turned on, the controller 11 reads a preliminary record processing program that executes processing illustrated in FIG. 10 from the ROM 11b and executes the program. The following describes the processing illustrated in FIG. 10 while description of any processing the same as the processing illustrated in FIGS. 2, 6, and 8 is simplified.

When the correct optical adapter 19 is mounted and the endoscope apparatus 1 becomes ready for performing endoscope examination through the adapter check processing (S1), a live image is displayed on the display 15.

After S1, the controller 11 executes image change amount determination processing of determining a change amount of a live image (S41).

At S41, the controller 11 calculates a change amount of the luminance value of each pixel between a current frame and a frame right before in a live image outputted to the display 15. This change amount is a change amount in the luminance value of each pixel between two continuous frames or a change amount in the luminance value of each pixel between two frames at each predetermined duration.

For example, when the user is pressing the distal end portion 2a of the insertion portion 2 into the examination target, an endoscope image changes, and thus the image has a large change amount. Or when the user releases a hand from the insertion portion 2 to perform another operation halfway through examination and the distal end portion 2a of the insertion portion 2 is at rest in the examination target, the image has no change amount or an extremely small change amount.

The controller 11 determines whether the change amount of the live image is within a predetermined range based on a result of the calculation at S41 (S42). When the change amount of the live image is not within the predetermined range (NO at S42), the process returns to S41.

When it is determined that the change amount of the live image is within the predetermined range based on the result of the calculation at S41 (YES at S42), the controller 11 starts recording of the live image in the sub recording unit 13b (S2) and performs display processing indicating "in preliminary recording" (S3).

That is, recording of an endoscope image (moving image) in the sub recording unit 13b is performed when the live image changes.

After S3, the controller 11 executes image change amount calculation processing the same as the processing at S41 (S43), and determines whether the change amount of the live image is within the predetermined range (S44). When the change amount of the live image is within the predetermined range (YES at S44), the process returns to S43.

At S44, when it is determined that the change amount of the live image is not within the predetermined range (NO at S44), the controller 11 ends the recording of the live image in the sub recording unit 13b (S5) and stops displaying "in preliminary recording" (S25).

After S25, when the endoscope apparatus 1 is turned off, the process ends. When the endoscope apparatus 1 is not turned off (NO at S4), the process returns to S41.

As described above, the processing at S41 and S43 configures an examination situation determination unit configured to determine a examination situation by the user. The controller 11 performs control to record a live image in the sub recording unit 13b based on the examination situation determined by the examination situation determination unit.

In the present embodiment, the examination situation determination unit of S41 and S43 is an image change amount calculation unit configured to calculate the change amount of an image acquired by the image pickup device 10.

The examination situation by the user is a state indicating whether the change amount of an image is within a predetermined range. When it is determined by the image change amount calculation unit that the change amount of the image is within the predetermined range, the controller 11 records a live image acquired by the image pickup device 10 in the sub recording unit 13b.

Note that the processing of recording of a still image and recording of a moving image in accordance with an instruction from the user during examination is the same as the processing in the first embodiment.

Figure 11:
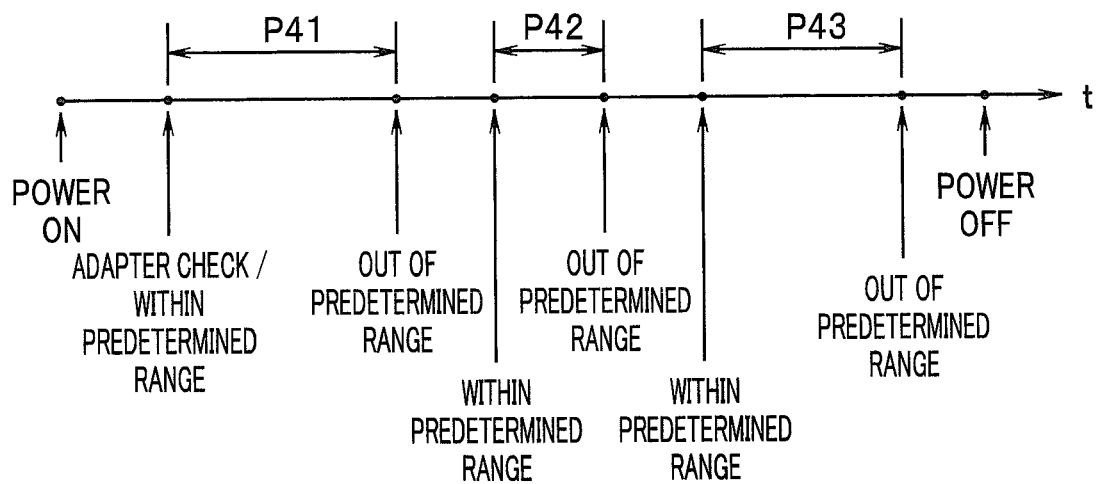
FIG. 11 is a time chart illustrating the duration of recording of an endoscope image (moving image) in the sub recording unit 13*b* until the endoscope apparatus 1 is turned off after the endoscope apparatus 1 is turned on according to the fourth embodiment of the present invention.

FIG. 11 is an exemplary time chart illustrating the duration of recording of an endoscope image (moving image) in the sub recording unit 13b until the endoscope apparatus 1 is turned off after the endoscope apparatus 1 is turned on.

As illustrated in FIG. 11, recording of an endoscope image in the sub recording unit 13b is started when the change amount of a live image is within the predetermined range after the power switch 18 of the endoscope apparatus 1 is turned on and the optical adapter 19 is checked as time t elapses. When the user interrupts examination, the change amount extremely decreases and the change amount of the live image becomes out of the predetermined range. Accordingly, the recording of an endoscope image in the sub recording unit 13b stops. Thus, recording of an endoscope image in the sub recording unit 13b is performed in a duration P41 until the change amount of the live image becomes not within the predetermined range after the change amount of the live image becomes within the predetermined range following the adapter check.

When the examination is resumed and the change amount of the live image is within the predetermined range, the live image is displayed on the display 15 and recording of an endoscope image in the sub recording unit 13b is resumed.

Thereafter, when the user interrupts the examination again or when the distal end portion 2a moves fast inside the examination target through an insertion operation of the insertion portion 2, the change amount of the live image becomes out of the predetermined range, and accordingly, recording of an endoscope image in the sub recording unit 13b stops. Thus, recording of an endoscope image in the sub recording unit 13b is performed in a duration P42 until the change amount of the live image becomes out of the predetermined range after the change amount of the live image becomes within the predetermined range.

Then, recording of an endoscope image in the sub recording unit 13b is performed until the change amount of the live image becomes out of the predetermined range after the change amount of the live image becomes within the predetermined range. Then, recording of an endoscope image in the sub recording unit 13b is not performed in a duration P43 until the endoscope apparatus 1 is turned off after the change amount of the live image becomes out of the predetermined range. A sum of the durations P41, P42, and P43 corresponds to the entire recording time during which an endoscope image as a moving image is preliminarily recorded in the sub recording unit 13b.

As described above, the above-described embodiment can provide an endoscope apparatus, an endoscope system, and an endoscope image recording method that allow check of an examination place without performing operation for observation again, for example, when recording of an image of the examination place is missed.

(Fifth Embodiment)

In the endoscope apparatus according to the first embodiment, preliminary recording of an endoscope image is started when the endoscope apparatus 1 is turned on and becomes ready for displaying a live image, and the preliminary recording of an endoscope image ends when the endoscope apparatus 1 is turned off and examination ends. However, in a fifth embodiment, preliminary recording of an endoscope image is not performed when manual recording instructed by the user is performed.

The endoscope apparatus according to the present embodiment has a similar configuration to the configuration of the endoscope apparatus 1 according to the first to fourth embodiments (FIG. 1). Thus, any identical component is denoted by an identical reference sign, and description thereof will be omitted, whereas any different configuration will be described.

Figure 12:
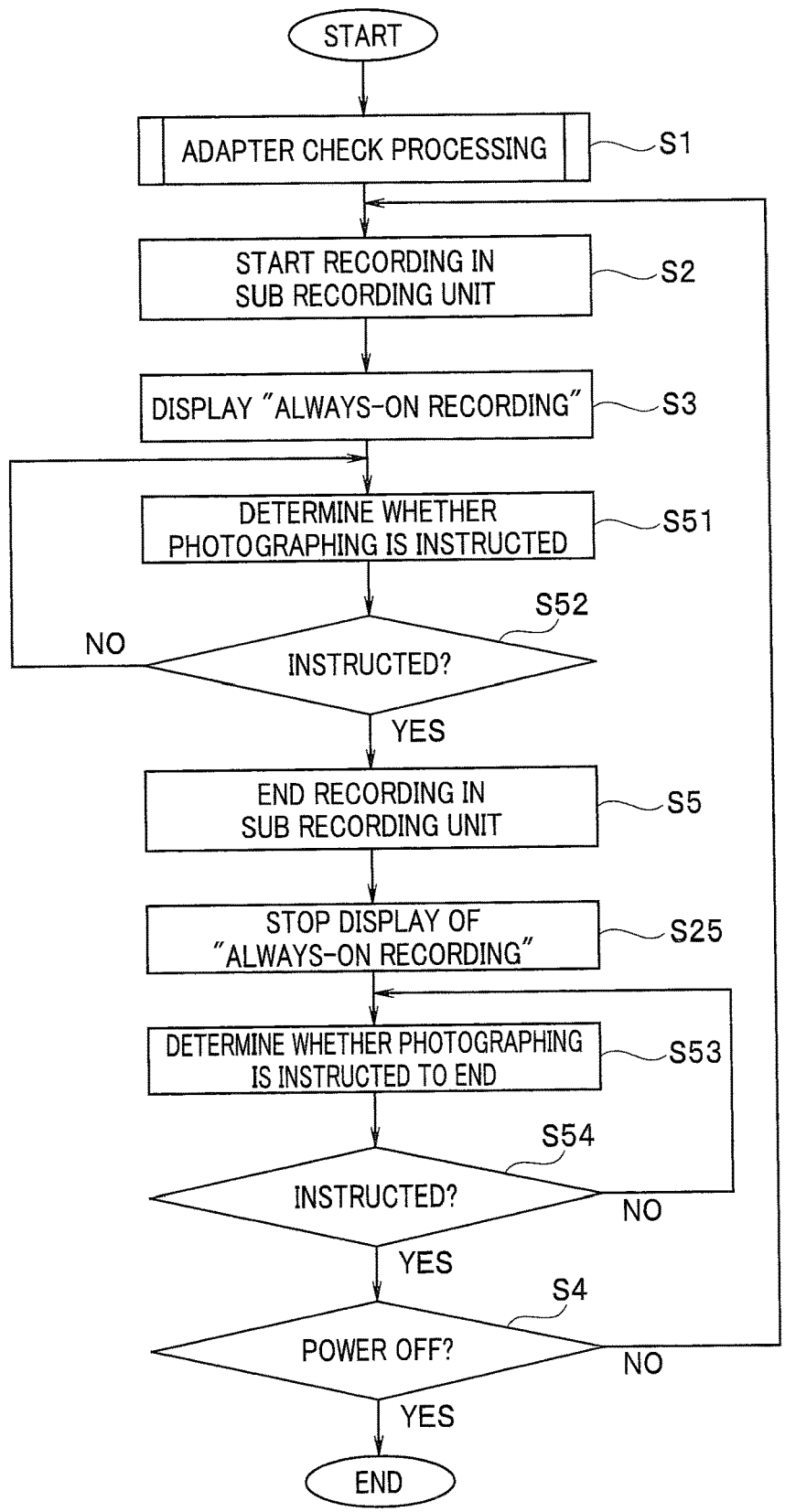
FIG. 12 is a flowchart illustrating an exemplary process of record processing in the sub recording unit 13*b* after the endoscope apparatus 1 is turned on according to a fifth embodiment of the present invention.

FIG. 12 is a flowchart illustrating an exemplary process of record processing in the sub recording unit 13b after the endoscope apparatus 1 is turned on according to the present embodiment.

When the power switch 18 of the endoscope apparatus 1 is turned on, the controller 11 reads an image time record processing program that executes the processing illustrated in FIG. 12 from the ROM 11b and executes the program. The following describes the processing illustrated in FIG. 12 while description of any processing the same as processing illustrated in FIGS. 2, 6, 8, and 10 is simplified.

When the correct optical adapter 19 is mounted and the endoscope apparatus 1 becomes ready for performing endoscope examination through the adapter check processing (S1), a live image is displayed on the display 15.

After S1, the controller 11 starts recording in the sub recording unit 13b (S2).

After S2, the controller 11 performs the display of "in preliminary recording" to notify the user (S3).

After S3, the controller 11 executes photographing start instruction determination processing of determining whether photographing is instructed by the user (S51). That is, whether photographing is manually instructed by the user is determined.

At S51, the controller 11 determines whether photographing is instructed by the user by determining whether the record button is operated through the operation unit 14. For example, recording of a moving image is started when the user presses the record button on the operation unit 14. Thus, the controller 11 can determine whether photographing is instructed by the user by detecting a state of operation on the record button.

When the controller 11 determines that photographing is not instructed by the user based on a result of the determination at S51 (NO at S52), the process returns to S51.

When it is determined that photographing is instructed by the user based on the result of the determination at S51, (YES at S52), the controller 11 ends recording of the live image in the sub recording unit 13b (S5) and stops the display of "in preliminary recording" (S25).

That is, preliminary recording of an endoscope image (moving image) in the sub recording unit 13b is stopped when photographing is started.

After S25, the controller 11 executes photographing end instruction determination processing of determining whether photographing is instructed to end by the user (S53). For example, the user can instruct recording of a moving image to end by operating the stop button, and thus whether the stop button is operated is determined at S53.

At S54, when it is determined that photographing is not instructed to end (NO at S54), the process returns to S53.

At S54, when it is determined that photographing is instructed to end (YES at S54), whether the endoscope apparatus 1 is turned off is determined (S4). When the endoscope apparatus 1 is turned off, the process ends. When the endoscope apparatus 1 is not turned off (NO at S4), the process returns to S2.

As described above, processing at SM and S53 configures an examination situation determination unit configured to determine a examination situation by the user. The controller 11 performs control to record a live image in the sub recording unit 13b based on the examination situation determined by the examination situation determination unit.

In the present embodiment, the examination situation determination unit of S51 and S53 is a record instruction determination unit configured to determine whether image recording is manually instructed by the user of the endoscope apparatus 1.

The examination situation by the user is a state indicating whether image recording is manually instructed by the user. When it is determined by the record instruction determination unit that image recording is manually instructed by the user, the controller 11 stops recording of a live image acquired by the image pickup device 10 in the sub recording unit 13b. When the image recording is instructed to stop by the user, the controller 11 records the live image in the sub recording unit 13b.

Note that the processing of recording of a still image and recording of a moving image in accordance with an instruction from the user during examination is the same as the processing in the first embodiment. Thus, an image is recorded in the main recording unit 13a until recording is instructed to end after the recording is manually instructed.

Typically, manual record instructions by the user include an instruction to record a still image and an instruction to record a moving image, but the instruction to record a still image is not handled by the processing illustrated in FIG. 12. It is determined whether recording of a moving image is manually instructed, and no preliminary recording in the sub recording unit 13b may be performed only when the manually instructing recording of a moving image is performed.

Figure 13:
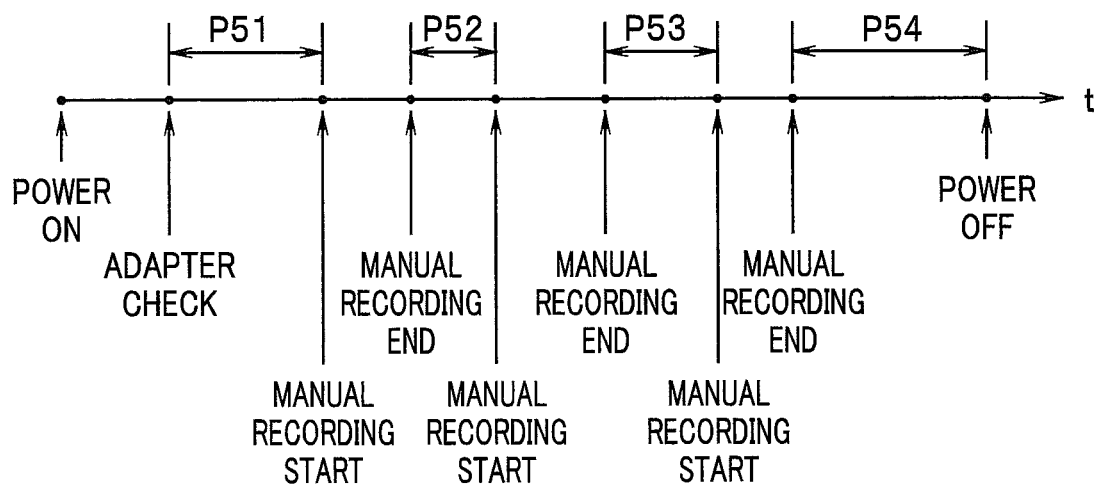
FIG. 13 is a time chart illustrating the duration of recording of an endoscope image (moving image) in the sub recording unit 13*b* until the endoscope apparatus 1 is turned off after the endoscope apparatus 1 is turned on according to the fifth embodiment of the present invention.

FIG. 13 is an exemplary time chart illustrating the duration of recording of an endoscope image (moving image) in the sub recording unit 13b until the endoscope apparatus 1 is turned off after the endoscope apparatus 1 is turned on.

As illustrated in FIG. 13, recording of an endoscope image in the sub recording unit 13b is performed until manual recording is instructed after the power switch 18 of the endoscope apparatus 1 is turned on and the optical adapter 19 is checked as time t elapses. When the user performs manual recording, an image is recorded in the main recording unit 13a, and thus image recording in the sub recording unit 13b is not performed. Thus, recording of an endoscope image in the sub recording unit 13b is performed in a duration P51 until manual recording is instructed after the adapter check.

When the manual recording is instructed to end by the user, recording of an endoscope image in the sub recording unit 13b is resumed.

Thereafter, when manual recording is instructed by the user again, the recording of an endoscope image in the sub recording unit 13b stops. Thus, recording of an endoscope image in the sub recording unit 13b is not performed in a duration until manual recording is instructed to end after the manual recording is instructed by the user. Recording of an endoscope image in the sub recording unit 13b is performed in durations P52 and P53 after the manual recording ends.

Recording of an endoscope image in the sub recording unit 13b is performed in a duration P54 until the endoscope apparatus 1 is turned off after the manual recording ends. A sum of the durations P51, P52, P53, and P54 corresponds to the entire recording time during which an endoscope image as a moving image is preliminarily recorded in the sub recording unit 13b.

As described above, the above-described embodiment can provide an endoscope apparatus, an endoscope system, and an endoscope image recording method that allow check of an examination place without performing operation for observation again, for example, when recording of an image of the examination place is missed.

The preliminary recording in the second to fifth embodiments described above is performed or interrupted in accordance with a predetermined condition, that is, the examination situation by the user. A generation state of such a condition may be recorded in association with a moving image recorded in the sub recording unit 13b in each above-described embodiment. In particular, when the preliminary recording is continuously performed as in the first embodiment and recording of such a generation state is performed, this record can be used to easily perform, for example, work of editing a preliminary record continuously recorded in accordance with a predetermined condition. When the record of the generation state of a condition is associated with, for example, a time code of a moving image recorded in the sub recording unit 13b, a situation of operation at examination can be determined at playback of a preliminarily recorded moving image.

For example, data on time of generation and deletion timings of each condition is stored, for example, by associating data of a start time and an end time of insertion of the insertion portion 2 with a time code of a file of a preliminarily recorded moving image or by associating data of a start time and an end time of measurement processing with a time code of a file of a preliminarily recorded moving image.

Note that when the generation state of each condition is recorded, information may be stored in a moving image file or may be recorded in another file and referred to at playback or editing.

In addition, not only the generation state of a condition described in the second to fifth embodiments but also information corresponding to occurrence of various events may be recorded in correspondence with a preliminary record. For example, information on change of an examination place or an examination condition may be recorded in association with a moving image recorded in the sub recording unit 13b.

For example, at recording of an endoscope image, the controller 11 can produce an examination folder in which the endoscope image is to be stored in the main recording unit 13a based on operation of the operation unit 14. The controller 11 can produce an examination folder having a hierarchical structure by including, in a folder name, various kinds of information on, for example, an examination object, an examination site, and an examination date. In such a case, it is possible to recognize, from the folder name, various kinds of information on, for example, the examination object, the examination site, and an examination condition.

At endoscope examination, for example, the user can specify an examination folder as a record destination folder through operation of the operation unit 14. For example, the user can check the record destination folder while watching a live image or a still image obtained by pressing the freeze button, and can easily change the record destination folder. When the user presses and operates the record button (REC button), an endoscope image as a still image or a moving image is recorded in the examination folder specified by the user.

Information indicating such change of the examination folder may be recorded as information indicating occurrence of an event in association with a moving image recorded in the sub recording unit 13b. This information indicates that the record destination folder in the main recording unit 13a is changed by the user, and for example, processing of skipping to an image part of a preliminary recorded moving image at a timing of the change of the record destination folder can be easily performed. As described above, when an examination folder is set in accordance with an examination place, an examination condition, and the like, for example, an endoscope image recorded for a certain examination place and a certain examination condition can be easily found from a preliminary recorded moving image by recording information indicating change of the examination folder in association with a moving image recorded in the sub recording unit 13b.

FIG. 14 is a diagram illustrating an exemplary image at playback of a preliminarily recorded moving image in the second to fifth embodiments. Even in preliminary recording, image data stored in the sub recording unit 13b can be read, played back, and displayed in a window different from a screen on which a live image is displayed. The user can perform fast-forward and rewind of an image stored in the sub recording unit 13b.

In this example, playback of a preliminarily recorded moving image can be performed by the endoscope apparatus 1, but may be performed by mounting the sub recording unit 13b as a memory card on another instrument such as a PC.

The display screen 15a of the display 15 displays a display region 31 for a playback image, a playback position information display portion 32 indicating a playback position in an entire recording time period, a fast-forward button 33, and a rewind button 34.

The playback position information display portion 32 includes, on a time line display portion 32a, a mark 35 indicating a playback time position at a current time point in the entire recording time period, and marks 36a and 36b each indicating a time position at which a predetermined condition or state is generated. The mark 35 moves right as a playback time elapses. For example, in the third embodiment, the mark 36a indicates that display of the menu screen is started, and the mark 36b indicates that display of the measurement screen is started.

The display screen 15a of the display 15 also displays skip buttons 37 and 38. The skip button 37 is a button for instructing skipping to a time position of a mark temporally after a current playback time position and then playback of the moving image. The skip button 38 is a button for instructing skipping to a time position of a mark temporally before the current playback time position and then playback of the moving image.

As described above, the first to fifth embodiments described above can provide an endoscope apparatus, an endoscope system, and an endoscope image recording method that allow check of an examination place without performing operation for observation again, for example, when recording of an image of the examination place is missed.

Note that the sub recording unit 13b in the first to fifth embodiments may be a ring buffer. Use of the ring buffer allows recording by overwriting to old data when the storage has no free space.

Note that, although a record destination of manual recording is the main recording unit 13a in the first to fifth embodiments, the controller 11 may change the record destination of manual recording from the main recording unit 13a to the sub recording unit 13b and record an image when the controller 11 cannot recognize the main recording unit 13a upon instruction of manual recording by the user.

Although the record destination of manual recording is the main recording unit 13a in the first to fifth embodiments, the controller 11 may check free space of the main recording unit 13a upon instruction of manual recording and change image data of a manually recorded image from the main recording unit 13a to the sub recording unit 13b when the main recording unit 13a does not have free space sufficient to record an image. This change is performed to prioritize image recording in response to a record instruction by the user.

In the second to fifth embodiments, preliminary recording is performed a plurality of times until the endoscope apparatus is turned off after the endoscope apparatus is turned on as time elapses in some case. In such a case, recording in the sub recording unit 13b may be performed in a record file format different for each time.

Although only a moving image is recorded in the sub recording unit 13b in each above-described embodiment, a microphone may be attached to the endoscope apparatus 1 to simultaneously record sound information.

For example, attention and warning messages and marks displayed on a moving image in a superimposed manner may be recorded in the sub recording unit 13b together with the moving image.

Each "unit" in the present specification is a concept corresponding to a function in the embodiments, and does not necessarily correspond to a particular piece of hardware or a software routine on a one-to-one basis. Thus, in the present specification, each embodiment is described above by assuming a virtual circuit block (unit) having each function of the embodiment. As long as characteristics of steps of each procedure in the present embodiments are maintained, an execution order steps may be changed, a plurality of the steps may be simultaneously executed, or the steps may be executed in a different order at each execution. In addition, all or part of the steps of each procedure in the present embodiments may be achieved by hardware.

The present invention is not limited to the above-described embodiments, and for example, various changes and modifications of the invention are possible without departing from the scope of the present invention.

The above and other objects, features and advantages of the invention will become more clearly understood from the following description referring to the accompanying drawings.

What is claimed is:
1. An endoscope comprising:
an insertion portion having a distal end portion;
an image sensor; and
a controller comprising hardware, the controller being configured to:

determine whether the distal end portion of the insertion portion is inserted in an examination target;

record, in a first storage, an image acquired by the image sensor as a first image when image recording is instructed by a user; and record, in a second storage, an image acquired by the image sensor as a second image when it is determined that the distal end portion of the insertion portion is inserted in the examination target.

2. The endoscope according to claim 1, wherein the controller is further configured to display the image acquired by the image sensor, wherein, if the second image is recorded in the second storage, the controller displays, on the display, one of a first mark or a first character for notifying a user that the second image is recorded in the second storage.

3. The endoscope according to claim 2, wherein if the first image that is a moving image is recorded in the first storage, the controller displays, on the display, one of a second mark or a second character for notifying the user that the first image is recorded in the first storage.

4. The endoscope according to claim 1, comprising at least one of the first storage for storing the first image and the second storage for storing the second image.

5. An endoscope system comprising:
the endoscope according to claim 1, and
at least one of the first storage and the second storage, the at least one of the first storage and the second storage being provided at a server connected to the controller through a network.

6. An endoscope comprising;
an insertion portion having a distal end portion;
an image sensor; and
a controller comprising hardware, the controller being configured to:
determine whether an image displayed on a display is a live image;
record, in a first storage, the image acquired by the image sensor as a first image when image recording is instructed by a user; and
record, in a second storage, the image acquired by the image sensor as a second image, when it is determined that the image displayed on the display is the live image.

7. An endoscope system comprising:
the endoscope according to claim 6, and
at least one of the first storage and the second storage, the at least one of the first storage and the second storage being provided at a server connected to the controller through a network.

8. An endoscope comprising:
an insertion portion having a distal end portion;
an image sensor; and
a controller comprising hardware, the controller being configured to:
calculate a change amount of an image acquired by the image sensor; and
record, in a first storage, the image acquired by the image sensor as a first image when image recording is instructed by a user; and
record, in a second storage, the image acquired by the image sensor as a second image if it is determined that the change amount of the image is within a predetermined range.

9. An endoscope system comprising:
the endoscope according to claim 8, and
at least one of the first storage and the second storage, the at least one of the first storage and the second storage being provided at a server connected to the controller through a network.

10. An endoscope apparatus comprising:
an operation unit through which recording of a first image acquired by an image sensor can be instructed;
a controller configured to:
record, in a first storage, the first image acquired by the image sensor when image recording is instructed through the operation unit; and
record, in a second storage, a second image acquired by the image sensor irrespective of whether the image recording is instructed through the operation unit; and
an examination situation determination unit configured to determine an examination situation by a user, wherein the controller performs control to perform recording in the second storage based on the examination situation determined by the examination situation determination unit; wherein
the examination situation determination unit is an insertion state determination unit configured to determine whether a distal end portion of an insertion portion of the endoscope apparatus is inserted in an examination target,
the examination situation is a state indicating whether the distal end portion is inserted in the examination target, and
the controller records, in the second storage, the second image acquired by the image sensor when it is determined by the insertion state determination unit that the distal end portion is inserted in the examination target.

11. The endoscope apparatus according to claim 10, wherein at least one of the first storage and the second storage is provided at a server connected through a network.

12. An endoscope apparatus comprising:
an operation unit through which recording of a first image acquired by an image sensor can be instructed;
a controller configured to:
record, in a first storage, the first image acquired by the image sensor when image recording is instructed through the operation unit; and
record, in a second storage, a second image acquired by the image sensor irrespective of whether the image recording is instructed through the operation unit; and
an examination situation determination unit configured to determine an examination situation by a user, wherein the controller performs control to perform recording in the second storage based on the examination situation determined by the examination situation determination unit; wherein
the examination situation determination unit is a live image determination unit configured to determine whether an image displayed on a display is a live image,
the examination situation is a state indicating whether the image displayed on the display is the live image, and
the controller records, in the second storage, the second image acquired by the image sensor when it is determined by the live image determination unit that the image displayed on the display is the live image.

13. The endoscope apparatus according to claim 12, wherein at least one of the first storage and the second storage is provided at a server connected through a network.

14. An endoscope apparatus comprising:
an operation unit through which recording of a first image acquired by an image sensor can be instructed;
a controller configured to:
- record, in a first storage, the first image acquired by the image sensor when image recording is instructed through the operation unit; and
- record, in a second storage, a second image acquired by the image sensor irrespective of whether the image recording is instructed through the operation unit; and an examination situation determination unit configured to determine an examination situation by a user, wherein the controller performs control to perform recording in the second storage based on the examination situation determined by the examination situation determination unit; wherein the examination situation determination unit is an image change amount calculation unit configured to calculate a change amount of the image acquired by the image sensor, the examination situation is a state indicating whether the change amount of the image is within a predetermined range, and the controller records, in the second storage, the second image acquired by the image sensor when it is determined by the image change amount calculation unit that the change amount of the image is within the predetermined range.

15. The endoscope apparatus according to claim 14, wherein at least one of the first storage and the second storage is provided at a server connected through a network.

* * * * *